United States Patent
Yoshikawa et al.

(10) Patent No.: US 7,642,299 B2
(45) Date of Patent: Jan. 5, 2010

(54) MULTI-FUNCTIONAL (METH) ACRYLATE COMPOUND, PHOTOCURABLE RESIN COMPOSITION AND ARTICLE

(75) Inventors: Yuji Yoshikawa, Annaka (JP); Koichi Higuchi, Annaka (JP); Masaaki Yamaya, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 117 days.

(21) Appl. No.: 11/602,991

(22) Filed: Nov. 22, 2006

(65) Prior Publication Data

US 2007/0116971 A1      May 24, 2007

(30) Foreign Application Priority Data

Nov. 24, 2005   (JP)   ............... 2005-338356

(51) Int. Cl.
C08G 77/20   (2006.01)
C08G 77/04   (2006.01)
C08G 77/14   (2006.01)
C08L 83/07   (2006.01)
C08L 83/06   (2006.01)
B32B 9/04    (2006.01)
B32B 27/30   (2006.01)
C08F 283/12  (2006.01)

(52) U.S. Cl. .................. 522/178; 528/32; 528/33; 524/588; 428/421; 428/447; 525/100; 525/479

(58) Field of Classification Search .......... 522/99, 522/178; 556/460; 524/588; 428/447, 421; 525/100, 479; 528/32, 33; 106/287.16
See application file for complete search history.

(56) References Cited

U.S. PATENT DOCUMENTS

| | | | | |
|---|---|---|---|---|
| 4,709,066 A | * | 11/1987 | Chapman | ............ 556/437 |
| 4,743,667 A | * | 5/1988 | Mizutani et al. | ............ 526/245 |
| 5,321,108 A | * | 6/1994 | Kunzler et al. | ............ 526/242 |
| 6,566,413 B1 | * | 5/2003 | Weinmann et al. | ............ 522/71 |
| 6,866,884 B2 | | 3/2005 | Hayashida et al. | |
| 2004/0002557 A1 | * | 1/2004 | Qian | ............ 523/113 |

FOREIGN PATENT DOCUMENTS

| | | | |
|---|---|---|---|
| EP | 811651 A2 | * | 12/1997 |
| JP | 11-503768 A | | 3/1999 |
| JP | 11/213444 A | | 8/1999 |
| JP | 11-293159 A | | 10/1999 |
| JP | 2002-190136 A | | 7/2002 |
| KR | 2004089035 A | * | 10/2004 |
| WO | WO-96/23828 A1 | | 8/1996 |

OTHER PUBLICATIONS

Derwent Summary of KR 2004-089035 A.*

* cited by examiner

*Primary Examiner*—Mark Eashoo
*Assistant Examiner*—Michael Pepitone
(74) *Attorney, Agent, or Firm*—Birch, Stewart, Kolasch & Birch, LLP

(57) ABSTRACT

A multi-functional (meth)acrylate compound containing at least three F atoms and at least three Si atoms per molecule is provided. A photocurable resin composition comprising the compound can endow support substrates with antifouling properties with respect to organic stains such as oil mist and fingerprints, without detracting from surface mar resistance.

7 Claims, No Drawings

MULTI-FUNCTIONAL (METH) ACRYLATE COMPOUND, PHOTOCURABLE RESIN COMPOSITION AND ARTICLE

CROSS-REFERENCE TO RELATED APPLICATION

This non-provisional application claims priority under 35 U.S.C. §119(a) on Patent Application No. 2005-338356 filed in Japan on Nov. 24, 2005, the entire contents of which are hereby incorporated by reference.

TECHNICAL FIELD

This invention relates to multi-functional (meth)acrylate compounds having antifouling capability, photocurable resin compositions which cure to substrates, upon exposure to radiation, to form cured coatings capable of imparting mar resistance to the substrate surface and having sufficient antifouling properties to prevent adhesion or allow for easy removal of fingerprints and debris, and articles having such coatings.

BACKGROUND ART

Synthetic resins including polymethyl methacrylate resins, polycarbonate resins, polystyrene resins, cyclic polyolefin resins, polyethylene terephthalate resins, and triacetyl cellulose resins have advantages including light weight, transparency and ease of working. Owing to such advantages, these synthetic resins are now utilized in a variety of articles including optical disks such as CD and DVD, display windows of liquid crystal and EL panels, and various functional films.

On use of such articles, their surface is often stained with many contaminants and marked with fingerprints. Since the adhesion of such stains and fingerprints is undesired, an appropriate surface treatment is sometimes conducted on the surface of optical data media for improving antifouling properties, reducing fingerprint receptivity or improving fingerprint removal. For example, a study has been made to carry out water-repellent or oil-repellent treatment on the surface of optical data media.

For improving the mar resistance of such media surface, it is a common practice to form a transparent, mar resistant hard coat on the writing and/or reading beam incident surface of media. The hard coat is formed by applying an actinic radiation-polymerizable/curable compound having at least two polymerizable functional groups such as (meth)acryloyl groups per molecule to the medium surface, and irradiating actinic radiation like ultraviolet radiation thereto for curing. However, since these hard coats are intended solely for mar resistance improvement, no antifouling effects with respect to dust and oil mist in the atmosphere or contaminants like fingerprints are expectable.

Known hard coats having antifouling capability to organic stains include, for example, hard coating compositions having crosslinkable fluorochemical surfactants added thereto as disclosed in JP-A 11-293159 and JP-A 2002-190136. These crosslinkable fluorochemical surfactants have polymerizable double bonds and crosslink with base resins in the hard coating compositions whereby the surfactants are fixed within the hard coats. JP-A 11-213444 and JP-A 11-503768 disclose application of fluoropolymers. However, coatings made of fluorinated material are low in strength because the fluorinated material is fixed within the coating interior as well. Reducing the amount of fluorinated material added can avoid a decline of strength at the sacrifice of antifouling property.

JP-A 2002-190136 discloses an optical data medium comprising a hard coat and a top coat of a silane coupling agent having a water or oil repellent group formed thereon, the medium having improved antifouling property on its surface. This approach is successful in imparting strength and antifouling property, but needs complex steps. It would be desirable to have a material which can impart strength and antifouling property by simply adding to a hard coat composition.

DISCLOSURE OF THE INVENTION

An object of the invention is to provide multi-functional (meth)acrylate compounds having antifouling capability; photocurable resin compositions which can endow support substrates with antifouling properties with respect to organic stains such as oil mist and fingerprints, especially sufficient antifouling properties to allow for easy removal of organic stains, without detracting from surface mar resistance; and articles having such coatings.

Making investigations on a surface protective layer, the inventor has found that a composition comprising a multi-functional (meth)acrylate compound containing at least three fluorine atoms and at least three silicon atoms per molecule, having the average compositional formula:

$$R_a R^f_b R^A_c SiO_{(4-a-b-c)/2}$$

wherein R is hydrogen or a methyl, ethyl, propyl, or phenyl group, $R^f$ is a fluorinated organic group, $R^A$ is an organic group containing a (meth)acrylic group, a is a number from 1 to 1.75, b is a number from 0.2 to 0.4, c is a number from 0.4 to 0.8, and a+b+c is from 2 to 2.7, and especially a composition comprising the multi-functional (meth)acrylate compound containing at least three fluorine atoms and at least three silicon atoms per molecule, another multi-functional (meth)acrylate compound, a radical initiator, and optionally metal fine particles forms a fully antifouling coating without detracting from mar resistance. Specifically, the composition comprising the multi-functional (meth)acrylate compound exhibits antifouling properties over a long term because the multi-functional (meth)acrylate compound is localized in a subsurface layer due to the siloxane skeleton's effect and fixed at the surface due to the inclusion of (meth)acrylic group.

Accordingly, the present invention provides a multi-functional (meth)acrylate compound, a photocurable resin composition, and a coated article, as defined below.

In one aspect, the invention provides a multi-functional (meth)acrylate compound containing at least three fluorine atoms and at least three silicon atoms per molecule, having the average compositional formula.

$$R_a R^f_b R^A_c SiO_{(4-a-b-c)/2}$$

Herein R is a hydrogen atom, methyl, ethyl, propyl, or phenyl group, $R^f$ is an organic group containing fluorine atoms, $R^A$ is an organic group containing a (meth)acrylic group, a is a number from 1 to 1.75, b is a number from 0.2 to 0.4, c is a number from 0.4 to 0.8, and a+b+c is from 2 to 2.7.

The preferred multi-functional (meth)acrylate compound is a branched siloxane having the general formula:

$$R^f SiR_k [OSiR_m (OR^A)_{3-m}]_{3-k}$$

wherein R, $R^f$ and $R^A$ are as defined above, m is 0, 1, or 2, and k is 0 or 1; or a cyclic siloxane having the general formula:

$$(R^f RSiO)(R^A RSiO)_n$$

wherein R, $R^f$ and $R^A$ are as defined above, and n is at least 2. In preferred embodiments, $R^A$ is linked to a silicon atom to form a Si—O—C linkage; and $R^f$ is a group of the formula: $C_xF_{2x+1}(CH_2)_p$— wherein x is an integer of 1 to 8 and p is an integer of 2 to 10 or a perfluoro polyether-substituted alkyl group.

In another aspect, the invention provides a photocurable resin composition having antifouling capability, comprising (a) 100 parts by weight of a multi-functional (meth)acrylate compound other than the following (b), (b) 0.01 to 5 parts by weight of the multi-functional (meth)acrylate compound defined above, (c) 0.1 to 10 parts by weight of a radical initiator, and optionally, (d) 5 to 200 parts by weight of metal fine particles.

In a further aspect, the invention provides an article comprising a cured coating of the photocurable resin composition.

BENEFITS OF THE INVENTION

A photocurable resin composition comprising a multi-functional (meth)acrylate compound containing at least three fluorine atoms and at least three silicon atoms per molecule is applied to an article or substrate requiring an antifouling layer on its surface and cured through radiation exposure to form a cured coating. The coating thus cured imparts mar resistance to the substrate surface, and has sufficient antifouling properties to prevent fingerprints and dust from adhering thereto and to allow for easy removal of such stains.

DESCRIPTION OF THE PREFERRED EMBODIMENTS

The multi-functional (meth)acrylate compound containing at least three fluorine atoms and at least three silicon atoms per molecule according to the invention has the following average compositional formula:

$$R_a R^f_b R^A_c SiO_{(4-a-b-c)/2}$$

wherein R is a hydrogen atom, methyl, ethyl, propyl, or phenyl group, $R^f$ is an organic group containing fluorine atoms, $R^A$ is an organic group containing a (meth)acrylic group, a is a number from 1 to 1.75, b is a number from 0.2 to 0.4, c is a number from 0.4 to 0.8, and a+b+c is from 2 to 2.7.

In the above formula, R is a hydrogen atom, methyl, ethyl, propyl, or phenyl group. The subscript a is a number from 1 to 1.75, preferably from 1 to 1.5. Compounds with a of less than 1 are difficult to synthesize in an industrially acceptable way whereas compounds with a of more than 1.75 fail to achieve both curing and antifouling properties.

$R^f$ is a fluorinated organic group, and preferably a group of the formula: $C_xF_{2x+1}(CH_2)_p$— wherein x is an integer of 1 to 8 and p is an integer of 2 to 10, or a perfluoro polyether-substituted alkyl group. Illustrative examples of $R^f$ include $CF_3C_2H_4$—, $C_4F_9C_2H_4$—, $C_4F_9C_3H_6$—, $C_8F_{17}C_2H_4$—, $C_8F_{17}C_3H_6$—, $C_3F_7C(CF_3)_2C_3H_6$—, $C_3F_7OC(CF_3)$ $FCF_2OCF_2CF_2C_3H_6$—, $C_3F_7OC(CF_3)FCF_2OC(CF_3)$ $FC_3H_6$—, and $CF_3CF_2CF_2OC(CF_3)FCF_2OC(CF_3)$ $FCONHC_3H_6$—. The subscript b is a number from 0.2 to 0.4, preferably from 0.2 to 0.25. Antifouling property declines at b of less than 0.2 whereas curing property degrades at b of more than 0.4.

$R^A$ is an organic group containing a (meth)acrylic group. Examples include $CH_2$=CHCOO—, $CH_2$=C(CH_3) COO—, $CH_2$=CHCOOC_3H_6—, $CH_2$=C(CH_3) COOC_3H_6—$CH_2$=CHCOOC_2H_4O—, and $CH_2$=C(CH_3) COOC_2H_4O—. More preferably, for ease of industrial synthesis, $R^A$ is linked to a silicon atom to form a Si—O—C linkage. The subscript c is a number from 0.4 to 0.8, preferably from 0.6 to 0.8. Curing property degrades at c of less than 0.4 whereas antifouling property declines at c of more than 0.8.

The sum a+b+c is from 2 to 2.7, preferably from 2 to 2.5. Compounds with a sum a+b+c less than 2 are unlikely to localize at the surface whereas compounds with a sum more than 2.7 fail to achieve both curing and antifouling properties.

The multi-functional (meth)acrylate of the invention contains per molecule at least three fluorine atoms and at least three silicon atoms, and preferably from 3 to 17 fluorine atoms and from 3 to 8 silicon atoms. Less than 3 fluorine atoms fail to achieve the desired antifouling property whereas less than 3 silicon atoms also fail to achieve the desired antifouling property probably because of insufficient surface localization.

Processes for the preparation of the multi-functional (meth)acrylate compound of the invention include, for example, addition reaction of a siloxane compound containing an organic group having at least three fluorine atoms and at least three Si—H groups with an allyl(meth)acrylate or the like; and dehydrogenation reaction between a siloxane compound containing an organic group having at least three fluorine atoms and at least three Si—H groups, and a (meth) acrylic compound containing an OH group such as hydroxyethyl acrylate. Of these processes, the addition reaction has a possibility that the (meth)acrylic group undergoes addition reaction as well, whereas the dehydrogenation reaction proceeds in the presence of a catalyst such as amines while keeping the (meth)acrylic group intact, so that the desired compound is easily obtained. In this sense, the dehydrogenation process is more preferred.

The siloxane structure may be either linear, branched or cyclic. Inter alia, branched and cyclic structures are particularly preferred because compounds of these structures are compatible with other multi-functional (meth)acrylate compounds to be described later, free of cissing, and likely to localize at the surface.

In one embodiment, the preferred multi-functional (meth) acrylate compounds of branched siloxane structure have the following general formula:

$$R^f SiR_k[OSiR_m(OR^A)_{3-m}]_{3-k}$$

wherein R, $R^f$, and $R^A$ are as defined above, m is 0, 1, or 2, more preferably m is equal to 2, and k is 0 or 1. Also the preferred multi-functional (meth)acrylate compounds of cyclic siloxane structure have the following general formula:

$$(R^f RSiO)(R^A RSiO)_n$$

wherein R, $R^f$, and $R^A$ are as defined above, and n is at least 2, more preferably from 3 to 5.

Illustrative examples of suitable multi-functional (meth)acrylate compounds include the following.

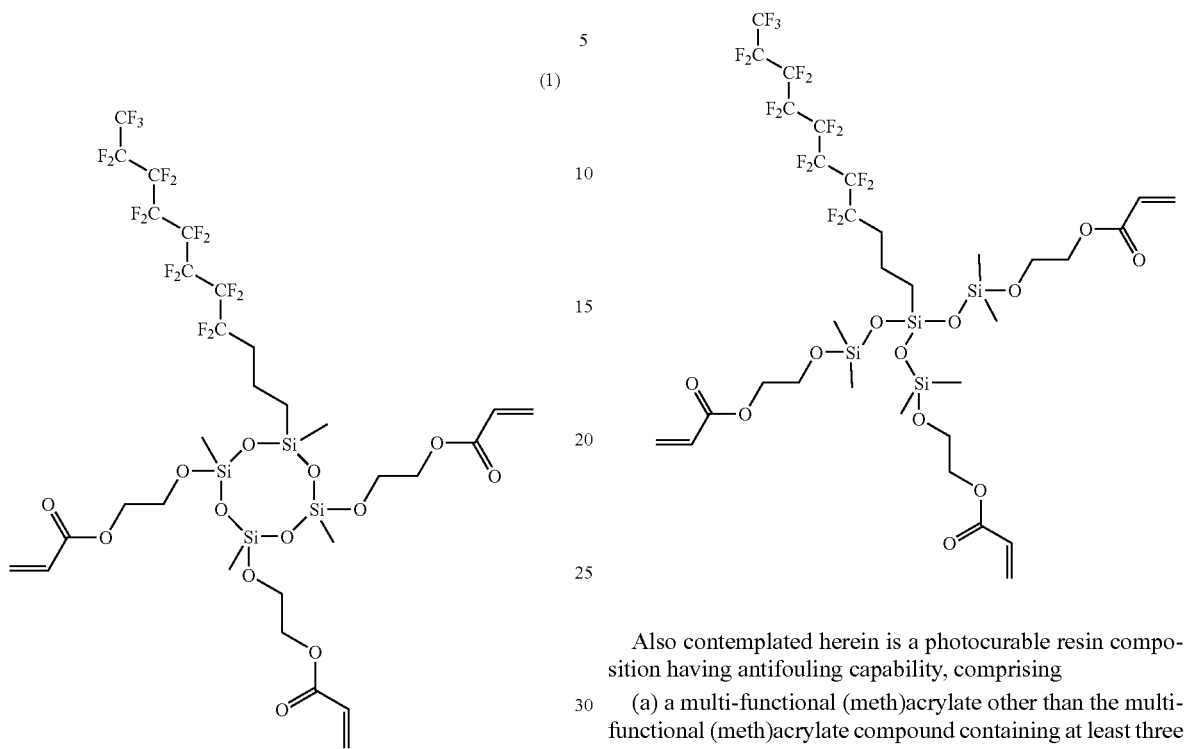

Also contemplated herein is a photocurable resin composition having antifouling capability, comprising (a) a multi-functional (meth)acrylate other than the multi-functional (meth)acrylate compound containing at least three fluorine atoms and at least three silicon atoms per molecule described above, (b) the multi-functional (meth)acrylate compound containing at least three fluorine atoms and at least three silicon atoms per molecule described above, (c) a radical initiator, and optionally, (d) metal fine particles.

(a) Multi-Functional (Meth)Acrylate

Component (a) of the composition is the base of a curable component and after curing, forms a matrix of the cured coating. Preferred are compounds containing at least two (meth)acrylic groups per molecule, examples of which include, but are not limited to, 1,6-hexanediol di(meth)acrylate, triethylene glycol di(meth)acrylate, ethylene oxide-modified bisphenol A di(meth)acrylate, trimethylolpropane tri(meth)acrylate, pentaerythritol tetra(meth)acrylate, ditrimethylolpropane tetra(meth)acrylate, dipentaerythritol hexa(meth)acrylate, pentaerythritol tri(meth)acrylate, 3-(meth)acryloyloxyglycerine mono(meth)acrylate, urethane acrylates, epoxy acrylates, ester acrylates and the like. These compounds may be used alone or in admixture.

(b) Multi-Functional (Meth)Acrylate Containing Fluorine and Silicon Atoms

Component (b) is a multi-functional (meth)acrylate compound containing at least three fluorine atoms and at least three silicon atoms per molecule described above, and serves to impart antifouling property.

Component (b) is included in an amount of 0.01 to 5 parts, preferably 0.05 to 3 parts by weight per 100 parts by weight of component (a). Less than 0.05 part by weight of component (b) is too small to provide antifouling property whereas more than 3 parts by weight of component (b) detracts from surface hardness.

(c) Radical Initiator

Component (c) may be selected from ordinary initiators such as acetophenone, benzoin, benzophenone, and thioxanthone initiators. Examples include Darocure® 1173, Irgacure® 651, Irgacure® 184, and Irgacure® 907 (all available from Ciba Specialty Chemicals).

Component (c) is included in an amount of 0.1 to 10 parts, preferably 0.5 to 8 parts by weight per 100 parts by weight of component (a). Less than 0.1 part by weight of component (c) results in under-curing whereas more than 10 parts by weight of component (c) detracts from surface hardness.

(d) Metal Fine Particles

Component (d) is metal fine particles, for examples, inorganic fine particles of metals or metalloids, fine particles of metal or metalloid oxides, and fine particles of metal or metalloid sulfides. Exemplary of the inorganic fine particles of metals or metalloids are Si, Ti, Al, Zn, Zr, In, Sn, Sb, etc. and composite oxides thereof, in fine particulate form. Besides oxides and sulfides of such metals and metalloids, selenides, tellurides, nitrides, carbides and the like are also useful. Particles surface coated with silica, alumina or the like are also acceptable. Suitable metal fine particles include fine particles of silica, alumina, zirconia, and titania, with silica fine particles being preferred. The addition of such metal fine particles enhances abrasion resistance.

Of the silica fine particles, those particles surface modified with a hydrolyzable silane compound having an actinic radiation-reactive group are more preferred. When actinic radiation is irradiated for curing of a hard coat, such reactive silica fine particles undergo crosslinking reaction whereby the particles are fixed within the polymer matrix.

Component (d) is included in an amount of 0 to 200 parts, preferably 0 to 150 parts by weight per 100 parts by weight of component (a). More than 200 parts by weight of component (d) may cause cracks. When used, component (d) is preferably included in an amount of at least 5 parts by weight.

In the photocurable resin composition of the invention, non-polymerizable diluent solvents, organic fillers, polymerization inhibitors, antioxidants, UV absorbers, light stabilizers, antifoaming agents, leveling agents and other additives may be included if necessary and insofar as they do not compromise the objects of the invention.

The photocurable resin composition of the invention may be prepared by mixing the components in accordance with a standard technique.

In forming a coating or film using the composition, any desired technique such as spin coating may be used. The coating preferably has a thickness of 0.5 to 30 μm.

The photocurable resin composition of the invention is cured by irradiating light, typically ultraviolet radiation. Well-known conditions for UV curing may be employed.

Specifically, the photocurable resin composition of the invention is applied and cured to an article to form a cured coating (antifouling layer) on its surface. Examples of the article which needs an antifouling layer on its surface include optical data media, optical lenses, optical filters, and antireflective coatings, as well as various display devices such as liquid crystal displays, CRT displays, plasma displays, and EL displays.

In a preferred embodiment, a cured coating of the photocurable resin composition of the invention is formed on optical data media such as read-only optical disks, optical recording disks, and magneto-optical recording disks, specifically on the writing and/or reading beam incident surface of media. The thus coated optical data media are improved not only in antifouling and lubricity, but also in mar resistance and abrasion resistance.

EXAMPLE

Synthesis Examples, Examples, and Comparative Examples are given below for further illustrating the invention, but are not intended to limit the invention. In the following Examples, the viscosity is as measured by a Cannon-Fenske capillary viscometer at 25° C., and the refractive index is as measured by a digital refractometer RX-7000α (Atago Co., Ltd.).

Synthesis Example 1

A reactor was charged with 69.4 parts by weight (0.1 mol) of a compound having the following formula (4), 36.5 parts by weight (0.315 mol) of 2-hydroxyethyl acrylate, and 111.9 parts by weight of toluene, which were mixed until uniform. Then 1.12 parts by weight (0.0126 mol) of N,N-diethylhydroxylamine was added as a catalyst. Thereafter reaction occurred for 8 hours at 70° C. The reaction mixture was washed with water, and then the toluene and the like were distilled off. The reaction product was identified as a compound of the following formula (1) by infrared absorption analysis, nuclear magnetic resonance analysis, and elemental analysis. The reaction product had a viscosity of 93.0 mm²/s and a refractive index of 1.4018.

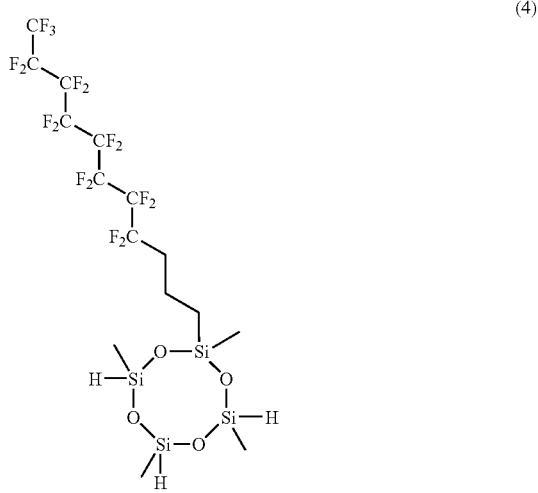

(4)

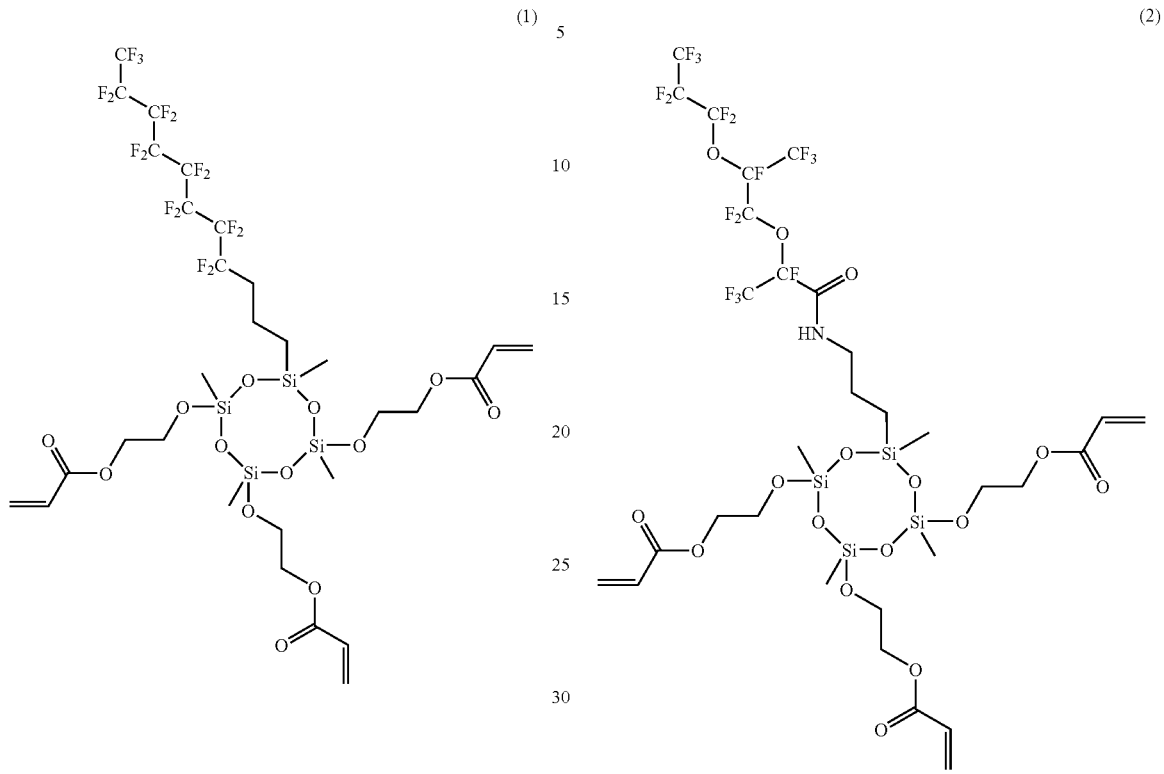

Synthesis Example 2

A compound having the formula (2) was obtained as in Synthesis Example 1 except that 75.7 parts by weight (0.1 mol) of a compound having the formula (5) was used instead of the compound having formula (4). The compound had a viscosity of 272 mm$^2$/s and a refractive index of 1.4031.

Synthesis Example 3

A compound having the formula (3) was obtained as in Synthesis Example 1 except that 70.8 parts by weight (0.1 mol) of a compound having the formula (6) was used instead of the compound having formula (4). The compound had a viscosity of 25.3 mm$^2$/s and a refractive index of 1.3985.

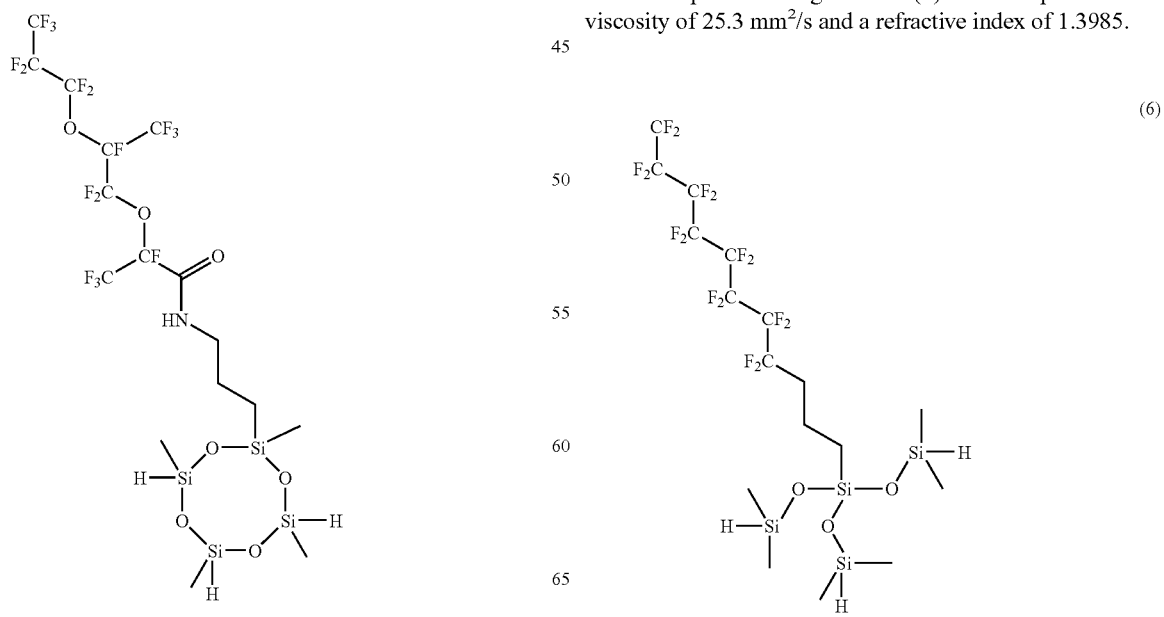

-continued

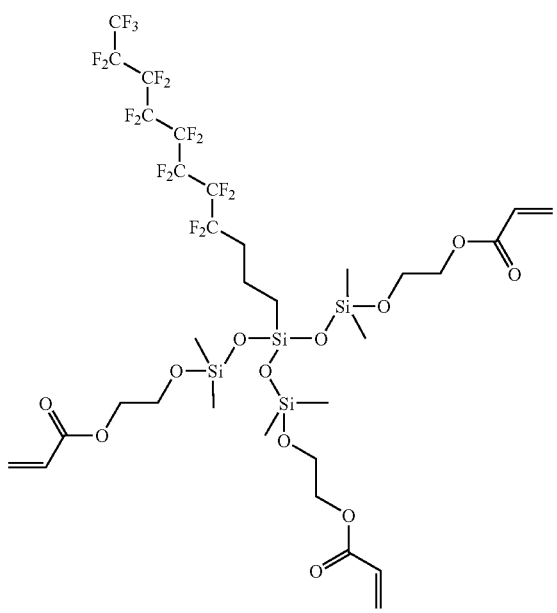

(3)

Example 1

40 parts by weight of silica treated with γ-acryloxypropyltrimethoxysilane, 40 parts by weight of trimethylolpropane triacrylate, 20 parts by weight of 1,6-hexanediol diacrylate, 0.5 part by weight of the compound of formula (1) obtained in Synthesis Example 1, and 5 parts by weight of Darocure® 1173 as a radical initiator were mixed. The resulting composition was applied onto a polycarbonate substrate by spin coating, and irradiated with UV light to form a coating having a thickness of 5 μm.

The coating formed was examined by the following tests. The results are summarized in Table 1.

I) Taber Abrasion Test

A haze change was measured after running an abrasion wheel CS-10F across the coating under a load 500 g over 100 revolutions, according to ASTM D1044.

II) Contact Angle of Oleic Acid

Measured using a contact angle meter CA-150X (Kyowa Interface Science Co., Ltd).

III) Marker Ink Wiping Property

The coating was marked with a felt pen. After 1 minute, the coating was wiped with gauze and observed whether any ink marks were left. Wiping was rated according to the following criteria.

◯: No traces of ink marks left

X: Traces of ink marks left

Example 2

An experiment was carried out as in Example 1 except that the compound of the formula (2) obtained in Synthesis Example 2 was used instead of the compound of formula (1).

Example 3

An experiment was carried out as in Example 1 except that the compound of the formula (3) obtained in Synthesis Example 3 was used instead of the compound of formula (1).

Comparative Example 1

An experiment was carried out as in Example 1, without adding the compound of formula (1).

Comparative Example 2

An experiment was carried out as in Example 1 except that octafluoropentyl acrylate was used instead of the compound of formula (1).

TABLE 1

| | Example | | | Comparative Example | |
|---|---|---|---|---|---|
| | 1 | 2 | 3 | 1 | 2 |
| Taber abrasion test | 7 | 8 | 5 | 5 | 7 |
| Contact angle of oleic acid, ° | 62 | 65 | 55 | UM | UM |
| Marker ink test | ◯ | ◯ | ◯ | x | x |

* UM: unmeasurable

Comparative Example 1 lacked antifouling property because the composition did not contain a fluorinated compound. Comparative Example 2 also lacked antifouling property because the composition contained fluorine, but not silicone so that the fluorinated compound did not localize at the surface.

Japanese Patent Application No. 2005-338356 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A multi-functional (meth)acrylate compound selected from the group consisting of the following formulae (I) and (II):

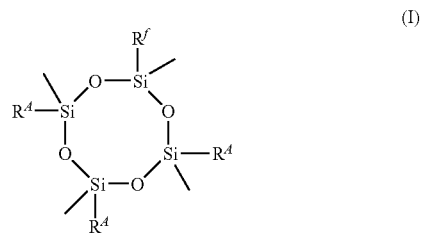

(I)

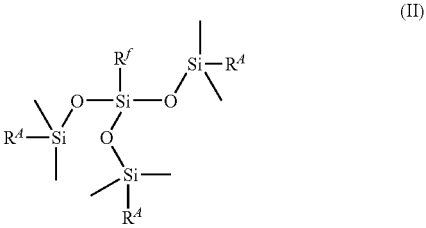

(II)

wherein $R^f$ is a fluorinated organic group selected from the group consisting of $C_xF_{2x+1}(CH_2)_p$— in which x is an integer of 4 to 8 and p is an integer of 2 to 10, $C_3F_7OC(CF_3)FCF_2OCF_2CF_2C_3H_6$—, $C_3F_7OC(CF_3)FCF_2OC(CF_3)FC_3H_6$—, and $CF_3CF_2CF_2OC(CF_3)FCF_2OC$ (CF$_3$)FCONHC$_3$H$_6$—, and R$^A$ is CH$_2$=CHCOOC$_2$H$_4$O— or CH$_2$=C(CH$_3$)COOC$_2$H$_4$O—.

2. A multi-functional (meth)acrylate compound selected from the group consisting of the following formulae (1) to (3):

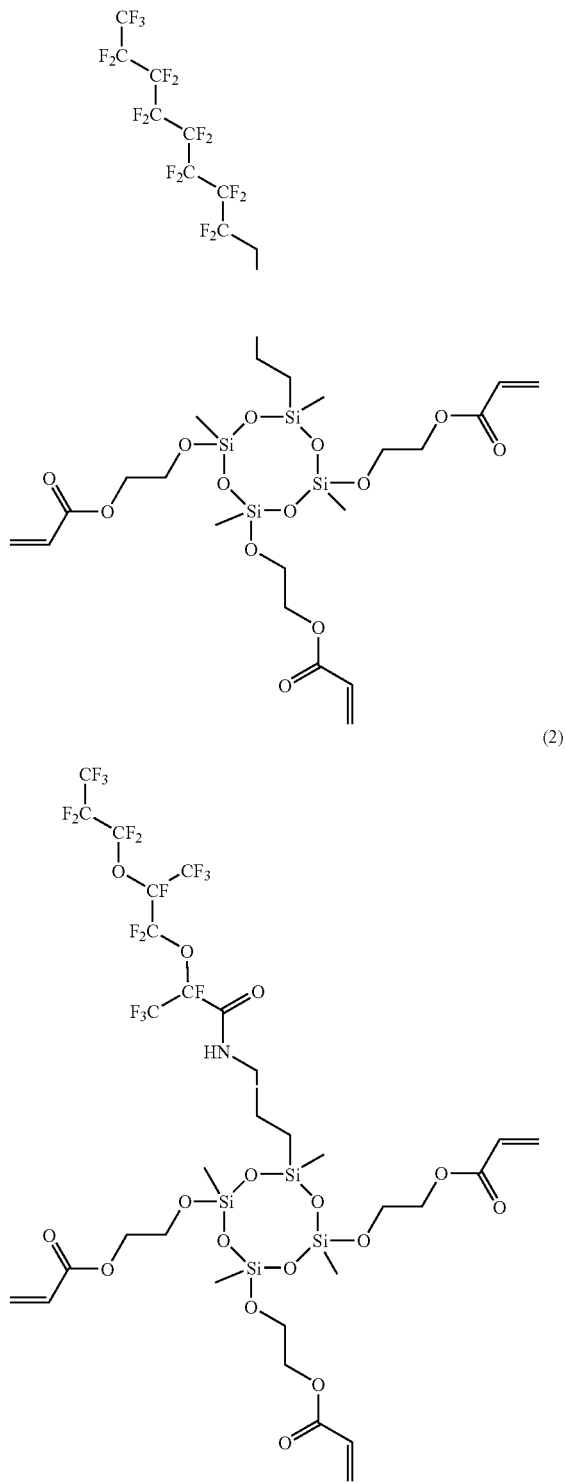

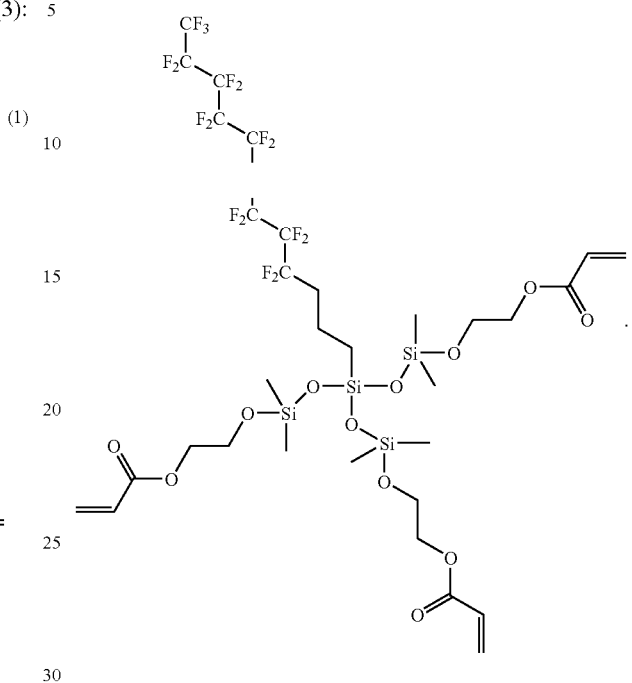

3. A photocurable resin composition having antifouling capability, comprising:
(a) 100 parts by weight of a multi-functional (meth)acrylate compound other than the following (b),
(b) 0.01 to 5 parts by weight of the multi-functional (meth)acrylate compound of claim 1 or 2, and
(c) 0.1 to 10 parts by weight of a radical initiator.

4. The photocurable resin composition of claim 3, further comprising (d) 5 to 200 parts by weight of metal fine particles.

5. An article comprising a cured coating of the photocurable resin composition of claim 3.

6. The article of claim 5, wherein the cured coating is formed as an antifouling layer on the surface of the article composed of a synthetic resin.

7. The composition of claim 5, wherein the multi-functional (meth)acrylate compound (b) is a branched siloxane having the general formula:

wherein R is a hydrogen atom, methyl, ethyl, propyl, or phenyl group, R$^f$ is a group of the formula: C$_x$F$_{2x+1}$(CH$_2$)$_p$— wherein x is an integer of 1 to 8 and p is an integer of 2 to 10 or a perfluoro polyether-substituted alkyl group, R$^A$ is an organic group containing a (meth)acrylic group, which organic group is selected from the group consisting of CH$_2$=CHCOO—. CH$_2$=C(CH3)COO—, CH$_2$=CHCOOC$_3$H$_6$—, CH$_2$=C(CH$_3$)COOC$_3$H$_6$—, CH$_2$=CHCOOC$_2$H$_4$O—, and CH$_2$=C(CH$_3$)COOC$_2$H$_4$O—, m is 2, and k is 0 or 1.

* * * * *